United States Patent [19]

Nilsson

[11] Patent Number: 4,700,702

[45] Date of Patent: Oct. 20, 1987

[54] INSTRUMENT FOR CUTTING TISSUES IN SURGERY

[76] Inventor: Tatiana Nilsson, Harpungränd 16, S-17547 Järfälla, Sweden

[21] Appl. No.: 806,645

[22] Filed: Dec. 9, 1985

[51] Int. Cl.$^4$ ............................................. A61F 17/32
[52] U.S. Cl. ........................................ 128/305; 30/380
[58] Field of Search ................. 128/751, 305, 304; 30/289, 272 R, 272 A, 284, 286, 380, 162, 154

[56] References Cited

U.S. PATENT DOCUMENTS

| | | |
|---|---|---|
| 3,734,652 | 5/1973 | Barnett . |
| 3,797,497 | 3/1974 | Crim et al. . |
| 3,835,859 | 9/1974 | Roberts et al. ...................... 128/305 |
| 3,882,737 | 5/1975 | Crim et al. . |
| 3,978,862 | 9/1976 | Morrison . |
| 4,203,444 | 5/1980 | Bonnell et al. . |
| 4,217,964 | 8/1980 | Eaton . |
| 4,246,902 | 1/1981 | Martinez ........................ 128/305 X |
| 4,274,414 | 6/1981 | Johnson . |
| 4,502,184 | 3/1985 | Karubian ............................... 30/380 |

Primary Examiner—Henry A. Bennet
Attorney, Agent, or Firm—Sandler & Greenblum

[57] ABSTRACT

The instrument comprises a motor, a means for coupling to the motor, two rods producing a link between the coupling means and the cutting tool. It also comprises a cutting tool and a sheath surrounding the cutting tool; an aperture is situated in the sheath to allow the cutting tool to be made level. The cutting tool is a guided flexible blade curved at the end, and this blade is driven by a backward and forward movement. The instrument can be used for cutting bony or cartilagineous tissues, or for cutting softer tissues, according to the shape of the sheath.

17 Claims, 11 Drawing Figures

INSTRUMENT FOR CUTTING TISSUES IN SURGERY

FIELD OF THE INVENTION

The present invention relates to an instrument for cutting tissues in surgery. It is suitable for cutting bony or cartilaginous tissues and is particularly suitable for use in surgery of the meniscus and more generally for the cavities of the body which are accessible from the exterior or through an opening of small dimension. It can also serve to remove or extirpate softer tissues, for example tumours, and to practice biopsies, notably on completion of analysis.

DESCRIPTION OF PRIOR ART

Numerous surgical instruments are known which are designed, for example, to operate on the meniscus of the knee, which function according to a principle of rotation. Examples of such instruments are given in the descriptions U.S. Pat. Nos. 4,274,414, 3,734,652, 4,203,444, 3,882,737, 4,217,964 and 3,797,497. They are used for cutting or piercing.

Instruments are also known which function according to an alternative principle. An example is given in the description U.S. Pat No. 3,978,862 which relates to a surgical saw.

With the above-mentioned instruments, it is, however, difficult to make true cuts. There is always a torn portion. Moreover, with a saw it is impossible to ensure the suction of the debris.

SUMMARY OF THE INVENTION

The object of the invention is to resolve the above-mentioned problems by making a true clean cut.

It relates to an instrument for cutting tissues in surgery, comprising a motor, a means for coupling to the motor, two rods producing a link between the coupling means and the cutting tool, as well as a cutting tool and a sheath surrounding the cutting tool; an aperture is situated in the sheath to allow the cutting tool to be made level. The cutting tool is a flexible guided blade curved at the end and the blade is driven in a backward and forward movement.

The guiding of the blade is preferably ensured by sliding in the sheath, the sheath being flexible or rigid.

A protection tube can surround the linking rods and thus in addition serves as an anchoring point for the sheath.

In another embodiment, the guiding by sliding can be completed by pressure on a freely rotating bearing arranged at the end of the sheath.

The motor driving the instrument can be electric or pneumatic. If this motor is of the rotating type, a transformation means positioned between the motor and the coupling means converts the rotating movement into a reciprocating or backward and forward movement. This transformation can be produced by a pin projecting from a female part, which surrounds a male shaft in which an oblique channel is situated, the pin being supported in the channel.

This backward and forward movement is advantageously transmittted on each linking rod which thus operates in cooperation. One rod pulls while the other pushes, this guaranteeing a good backward and forward motion of the flexible blade and correctly maintaining its tension.

The aperture arranged in the sheath surrounding the cutting blade can be in a lateral position or at the end. The position of this aperture can be adjusted in relation to a gripping handle which is fixed onto the surgical instrument itself and allows the surgeon to hold and guide this instrument.

The above description easily shows that constitutive elements of small dimensions and of small diameter can be used which allows the instrument to have very small dimensions.

As an accessory, the instrument can comprise a fastening receiving a hollow tube arranged parallel to the rods and to the sheath. This tube flattens and opens in the form of a spoon at its end, in such a manner as to form a cavity where the cutting debris will be collected. The debris is then withdrawn by suction through the hollow tube.

BRIEF DESCRIPTION OF THE DRAWINGS

The invention will be better understood by referring to the attached drawings, provided as non-limiting examples. In these drawings.

DETAILED DESCRIPTION OF THE INVENTION

Figure 1:
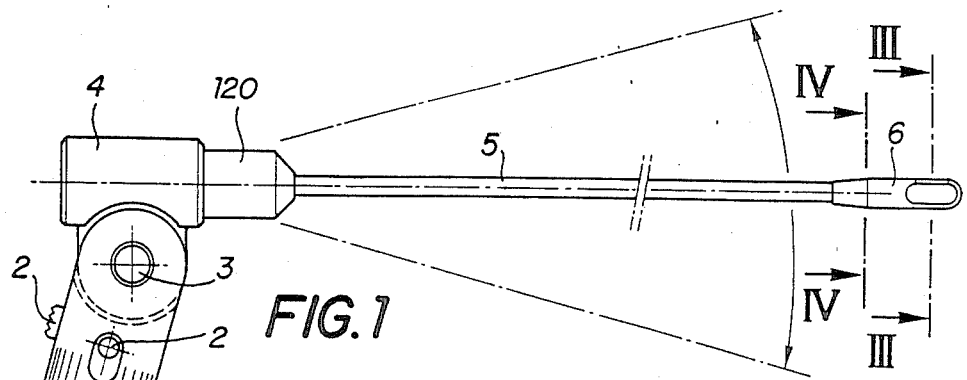
FIG. 1 is a general view of a surgical instrument according to the invention.

As can be seen in FIG. 1, the surgical instrument comprises a handle 1 in which an electric or pneumatic motor, not shown, is situated. The handle 1 can also contain means for feeding the motor, for example batteries or accumulator batteries. Control means 2 allow the motor to be set in motion, stopped and the speed thereof to be controlled.

This handle 1 is fixed to a supporting structure 4 by an axle 3 allowing the handle 1 to rotate at will about the supporting structure 4. This axle 3 comprises a brake, not shown, allowing the handle 1 to be locked in the desired position, up to and including a position of the instrument in complete alignment.

In the interior of the supporting structure 4 is, for example, a coupling means of a standard type (not shown). Other means can also be positioned in the interior of the supporting sturcture 4; if the motor is of the rotating type, a device transforming the rotating movement into an alternating backward and forward movement is arranged in this supporting structure 4.

At the exit of the supporting structure 4 is a tube 5 designed to surround and to guide two rods producing a link between the coupling means and a sheath 6 containing the cutting blade.

Figure 2:
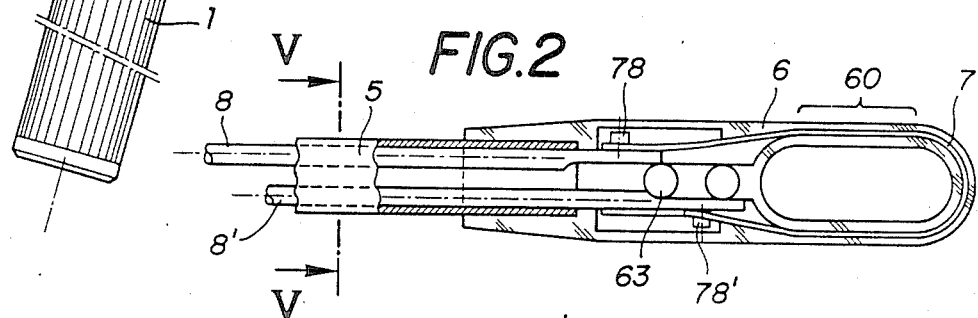
FIG. 2 is a detailed view of the end in section showing the flexible blade.
Figure 3:
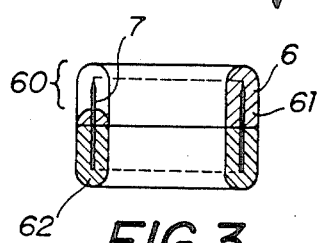
FIG. 3 is a view in section of FIG. 1, along the axis III—III.
Figure 4:
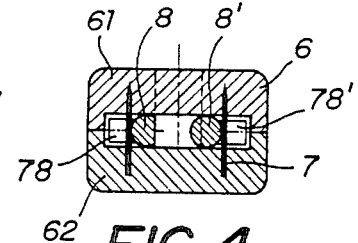
FIG. 4 is a view in section of FIG. 1, along the axis IV—IV.
Figure 5:
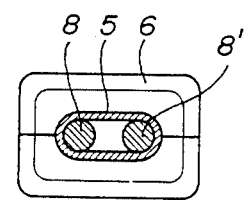
FIG. 5 is a view in section of FIG. 2, along the axis V—V.

As can be seen in more detail in FIG. 2, the sheath 6 surrounds and guides the cutting blade 7 while curving at the end thereof. This blade 7 is fixed to two linking rods 8, 8' by two fixing pins 78, 78'. An aperture 60 is situated in the sheath 6 in such a manner as to level the blade 7 which thus comes into contact with the tissues to be cut.

As can be seen in still more detail in FIGS. 3 to 6, the sheath is in fact composed of two sections 61 and 62 which fit into each other and are maintained firmly in this position by clipping elements 63. This structure in two sections securing one to the other allows the blade 7 to be installed in the interior of its sheath.

The sheath or tip 6 can be of any shape, straight, bent, curved, at 90°, in a W, etc. but without a sharp edge allowing certain parts of the body to which access is difficult to be reached more easily. In fact, this sheath can be formed as required according to the nature of the operation and the requirements of the surgeon. The possibility of numerous forms allows a good fit to the shape of the cavity to be operated on.

Figure 7:
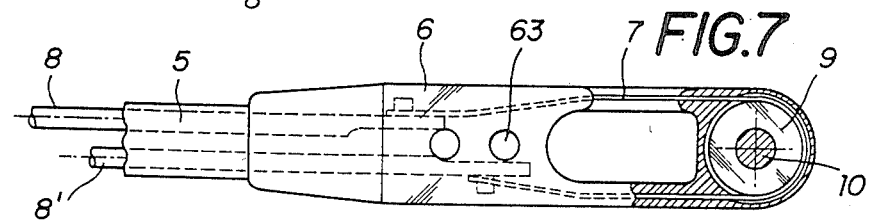
FIG. 7 is a view in partial section corresponding to FIG. 2, in another embodiment.

In the embodiment shown in FIG. 7, the cutting blade 7 is always guided by the sheath 6, but, in order to improve guiding in the end region, it rotates on a freely rotating bearing 9 about an axle 10.

During the operation, the surgeon holds the instrument by the handle 1 and carried out a movement with it which is analogeous to that of the cutter bringing the cutting blade 7 into contact with the section to be cut off at the level of the aperture 60. The cutting blade 7 is driven by a backward and forward movement, the cut is clean and the cutting movement imparted by the instrument allows the easy disengagement of the debris.

Figure 6:
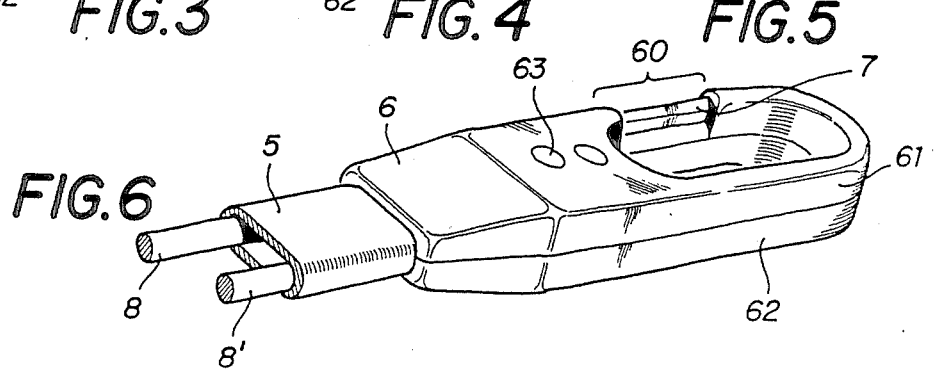
FIG. 6 is a perspective view of the end with the cutting blade, corresponding to FIG. 2.

The cutting blade 7 can be made level by the aperture 60 on a section of it height, for example on half the height as shown in FIG. 6. It is possible, however, to position the blade 7 at a smaller section or a larger section of its height, by opening the sheath in an appropriate manner.

It is worthwhile to deliver the sheath 6 in an uncut state, without an aperture with a tool allowing the aperture 60 to be cut open at the moment of use. The surgeon can thus position it as he wishes on the whole periphery of the sheath, with the width and height which suits him the best.

The instrument shown in FIGS. 2,6 and 7 can be used, for example, in open surgery of the bony or cartilaginous tissues, but is particularly interesting for surgery under arthroscopic control. The meniscus, the nose, the ears and as a general rule any cavity of the human or animal body can thus be operated on.

Figure 8:
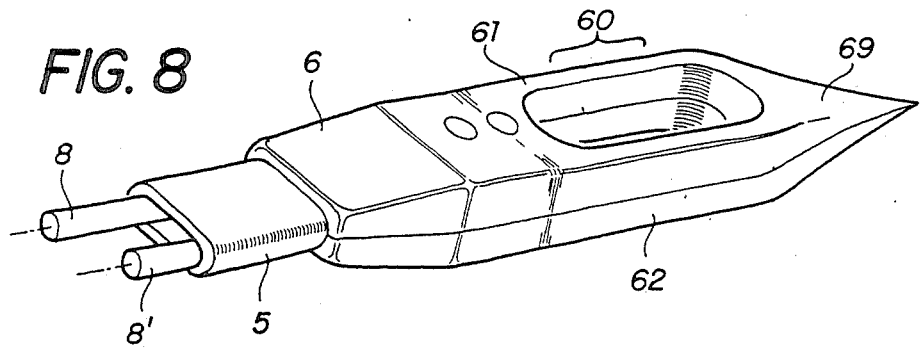
FIG. 8 is a view corresponding to that of FIG. 5 in another embodiment.

In FIG. 8, another embodiment is shown which is more specially adapted to surgery of softner tissues than the bony or cartilaginous tissues. The sheath or tip 6 is extended by a projection 69 in the form of a point, having a substantially concial, straight or concave geometry, which is designed to penetrate these tissues and separate them for positioning the cutting blade exactly at the position to be operated on. A tumour can thus be extirpated or tissue removed for carrying out a biopsy on completion of an analysis or a diagnosis, for example. There again, the aperture 60 is produced as desired by the surgeon.

Figure 9:
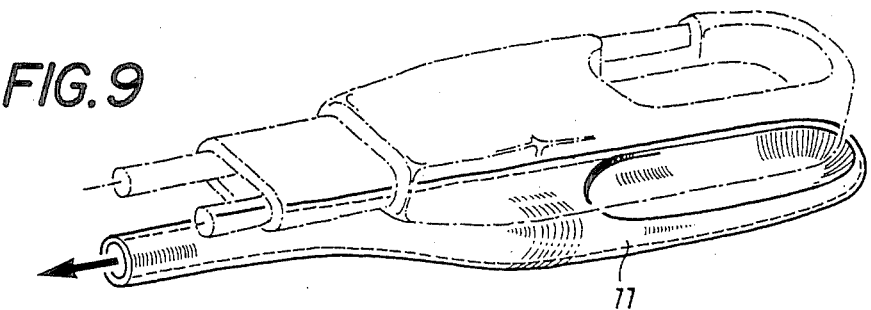
FIG. 9 represents a suction accessory.

In FIG. 9, a complementary tube is shown having an end in the form of a spoon 11 producing a cavity and forming a receiver for the cutting debris which collects there and which will be withdrawn through the tube by suction, according to the direction of the arrow. This spoon 11 is positioned below the assembly to collect the debris by gravity and eliminate it from the operating field. When cutting bony or cartilagineous tissues this debris is generally produced in the form of slivers.

Figure 10:
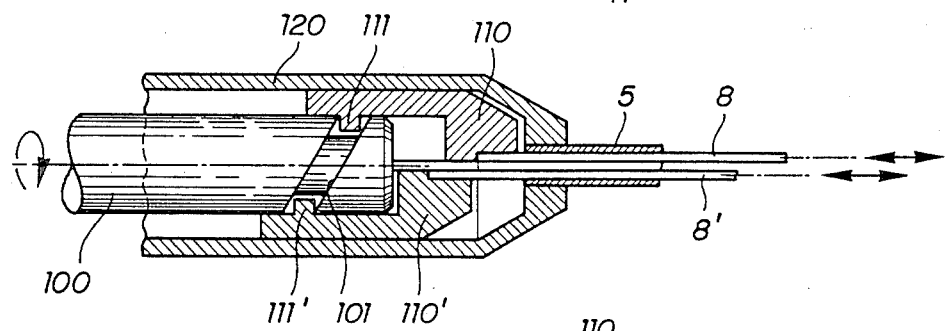
FIGS. 10 and 11 show the means for transforming the rotating movement imparted by the motor into a backward and forward movement.

In FIG. 10, which is a sectional view, it can be seen how the rotating movement imparted by the motor is transformed into a backward and forward movement applied on the linking rods 8, 8'. Indeed, the motor shaft 100 comprises a channel in a recess 101, which is oblique in relation to the axle of this shaft. A female recessed shell-shaped section surrounds the shaft 100 and is divided into two sections 110,110' according to an equatorial plane. In the interior of the two semi-shells 110, 110', two raised pins 111, 111' are positioned which are supported in the oblique channel 101.

The two linking rods 8, 8' are respectively fixed on the two sections 110, 110'. These rods slide into the sheath 5, shown only at its point or origin.

Figure 11:
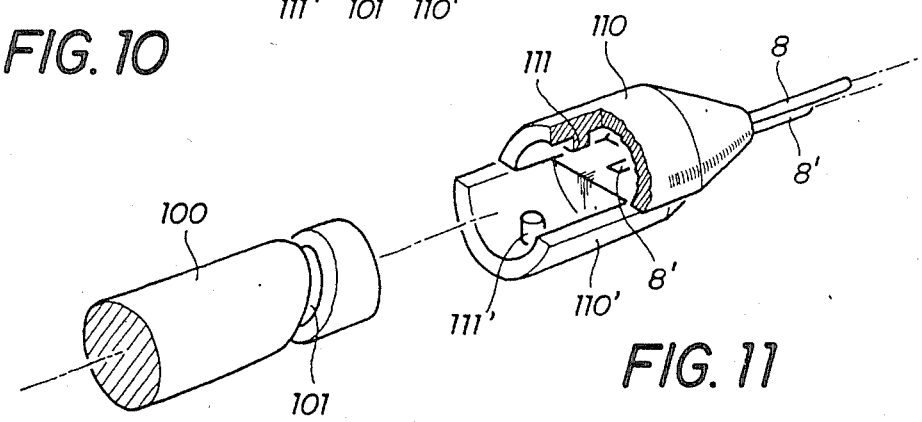

All this can also be easily seen in FIG. 11, which is an exploded perspective view, in which the motor shaft 100 and the female section in two semi-shell sections 110, 110' are shown disengaged from each other.

From these two Figures, it can be easily understood that the rotation of the motor shaft 11 induces a backward and forward movement at the level of the pins 111, 111' and consequently at the level of the two semi-shells 110, 110'. Finally, the backward and forward movement is transmitted to the linking rods 8, 8'.

The assembly is positioned in a housing 120 as shown in FIGS. 1 and 10.

The linking rods 8, 8' in turn impart the backward and forward movement to the cutting blade 7, as can be easily seen by referring to FIG. 2.

I claim:

1. A surgical instrument for cutting tissue comprising:
    (a) motor means;
    (b) a cutting tool comprising of flexible arcuate blade extending along a longitudinal direction, wherein a portion of said blade is exposed along a portion of said longitudinal direction;
    (c) means for coupling said motor means to said cutting tool wherein said motor means and said coupling means comprise means for reciprocating said blade in said longitudinal direction
    (d) a sheath surrounding said cutting tool;
    (e) two rods for linking the coupling means and the cutting tool;
    wherein said sheath has an aperture therein to expose said portion of said blade, wherein guiding of the blade is assured by the sheath.

2. An instrument for cutting tissues in surgery comprising:
    (a) a motor means;
    (b) a cutting tool comprising an arcuate blade having first and second ends;
    (c) means for pulling said first and in a first longitudinal direction; and
    (d) means for pushing said second end in said first longitudinal direction, wherein said motor means comprises means for actuating said pulling and pushing means, said means for pulling further comprising means for pushing said first and in a second longitudinal direction opposite from said first longitudinal direction, wherein said pushing means comprises means for pulling said second end in said second longitudinal direction;

(e) a sheath surrounding the cutting tool, wherein said pushing and pulling means each comprise a rod linking the motor means and the cutting tool, wherein said sheath has an aperture therein to expose a portion of said blade.

3. An instrument according to claim 1, wherein said blade slides in said sheath, wherein the guiding of the blade in the sheath is ensured by said sliding.

4. An instrument according to claim 1, further comprising a freely rotating bearing at one end of said sheath, wherein the guiding of the blade in the sheath is ensured by said freely rotating bearing.

5. An instrument according to claim 1, further comprising a plurality of clipping elements, wherein the sheath comprises two sections which fit into each other by means of said clipping elements.

6. An instrument according to claim 1, wherein said coupling means transmits reciprocating movement to said two rods such that one rod pulls one portion of said cutting tool in one direction while the other rod pushes another portion of said cutting tool in said one direction.

7. An instrument according to claim 1 further comprising a hollow tube extending parallel to the rods and to the sheath, which surrounds said rods and terminates by flattening and opening in the form of a spoon allowing the cutting waste from said cut tissues to be collected, and withdrawn by suction through the hollow tube.

8. An instrument according to claim 1 further comprising a projection on said sheath and ending in a point, wherein the sheath is extended by said projection.

9. An instrument according to claim 1, wherein the motor is a rotating motor producing rotating movement, wherein said instrument further comprises means for transforming the rotating movement of the motor into reciprocating movement wherein said transformation means is positioned between the motor and the coupling means.

10. An instrument according to claim 9, wherein the transformation means comprises:

a rotatably driven motor shaft provided with an oblique channel in a recess in said shaft; and a female recessed section surrounding the shaft, comprising two semi-shells sliding on each other in an equatorial plane and each joined to one of said two rods respectively, each semi-shell comprising a raised pin in the interior thereof which is supported in the oblique channel.

11. The instrument according to claim 2, wherein said pulling and pushing means push and pull said blade simultaneously.

12. The instrument according to claim 2 further comprising a freely rotating bearing at the end of said sheath for guiding the blade in the sheath.

13. An instrument according to claim 2 further comprising a plurality of clipping elements, wherein the sheath comprises two sections which fit into each other by means of said clipping elements.

14. An instrument according to claim 1 further comprising a hollow tube extending parallel to the rods and to the sheath, which encloses said rods and terminates by flattening and opening in the form of a spoon allowing cutting waste from said tissue to be collected and withdrawn by suction through the hollow tube.

15. The instrument according to claim 2, wherein the motor is a rotating motor and said instrument further comprises means for transforming the rotating movement of the motor into reciprocating movement for reciprocating said rods, wherein said transforming means is positioned between the motor means and the rods.

16. The instrument according to claim 15, wherein the transforming means comprises:

a rotatably driven motor shaft provided with an oblique channel in a recess in the shaft; and a female recessed section surrounding the shaft comprising two semi-shells sliding on each other in an equatorial plane and each joined to one of the rods, each semi-shell having a raised pin in the interior thereof which is supported in the oblique channel.

17. The instrument defined by claim 1 wherein said blade has an upper cutting edge extending in said longitudinal direction.

* * * * *